United States Patent
Das et al.

(10) Patent No.: US 10,827,981 B2
(45) Date of Patent: Nov. 10, 2020

(54) SYSTEM AND METHOD FOR EVALUATING A COGNITIVE LOAD ON A USER CORRESPONDING TO A STIMULUS

(71) Applicant: Tata Consultancy Services Limited, Mumbai (IN)

(72) Inventors: Diptesh Das, Kolkata (IN); Debatri Chatterjee, Kolkata (IN); Arijit Sinharay, Kolkata (IN); Aniruddha Sinha, Kolkata (IN)

(73) Assignee: Tata Consultancy Services Limited, Mumbai (IN)

( * ) Notice: Subject to any disclaimer, the term of this patent is extended or adjusted under 35 U.S.C. 154(b) by 302 days.

(21) Appl. No.: 15/023,314

(22) PCT Filed: Sep. 12, 2014

(86) PCT No.: PCT/IB2014/064466
§ 371 (c)(1),
(2) Date: Mar. 18, 2016

(87) PCT Pub. No.: WO2015/040532
PCT Pub. Date: Mar. 26, 2015

(65) Prior Publication Data
US 2016/0242699 A1  Aug. 25, 2016

(30) Foreign Application Priority Data
Sep. 19, 2013  (IN) .......................... 3025/MUM/2013

(51) Int. Cl.
*A61B 5/0484* (2006.01)
*A61B 5/00* (2006.01)
(Continued)

(52) U.S. Cl.
CPC ............ *A61B 5/7267* (2013.01); *A61B 5/048* (2013.01); *A61B 5/0476* (2013.01);
(Continued)

(58) Field of Classification Search
None
See application file for complete search history.

(56) References Cited

U.S. PATENT DOCUMENTS

| 8,374,687 B2 | 2/2013 | Mathan et al. |
| 2010/0100001 A1 | 4/2010 | Aguilar et al. |

(Continued)

OTHER PUBLICATIONS

Besserve et al. Prediction of performance level during a cognitive task from ongoing EEG oscillatory activities. Clinical Neurophysiology 119 (2008) 897-908.*

(Continued)

*Primary Examiner* — Etsub D Berhanu
(74) *Attorney, Agent, or Firm* — Finnegan, Henderson, Farabow, Garrett & Dunner LLP

(57) ABSTRACT

System and method for evaluating a cognitive load on a user, corresponding to a stimulus is disclosed. Electroencephalogram (EEG) data corresponding to the stimulus of a user is received. The stimulus corresponds to a mental task performed by the user. The EEG data is split into a plurality of slots. A slot of the plurality of slots comprises a subset of the EEG data. One or more EEG features are extracted from the subset of the EEG data. The one or more EEG features are represented in one of a frequency domain and a time domain. A plurality of data points present in the one or more EEG features is grouped into two or more clusters using an unsupervised learning technique. The two or more clusters comprise one or more data points of the plurality of data points. The one or more data points correspond to a level of the cognitive load.

12 Claims, 5 Drawing Sheets

(51) Int. Cl.
 A61B 5/0476 (2006.01)
 A61B 5/048 (2006.01)
(52) U.S. Cl.
 CPC ............ *A61B 5/0484* (2013.01); *A61B 5/725* (2013.01); *A61B 5/7264* (2013.01)

(56) References Cited

U.S. PATENT DOCUMENTS

| | | |
|---|---|---|
| 2011/0159467 A1 | 6/2011 | Peot et al. |
| 2011/0289030 A1 | 11/2011 | Lu et al. |
| 2012/0071780 A1* | 3/2012 | Barachant ......... A61B 5/04012 600/544 |
| 2012/0108997 A1* | 5/2012 | Guan ................ A61B 5/04014 600/545 |
| 2012/0235912 A1 | 9/2012 | Laubach |

OTHER PUBLICATIONS

Srinivasa et al. Generic Feature Extraction for Classification using Fuzzy C-Means Clustering. 2005 3rd International Conference on Intelligent Sensing and Information Processing.*

Chatterjee et al. EEG-Based Fuzzy Cognitive Load Classification during Logical Analysis of Program Segments. 2013 IEEE International Conference on Fuzzy Systems.*

Das et al. Stabilization of Cluster Centers over Fuzziness Control Parameter in Component-wise Fuzzy c-Means Clustering. 2013 IEEE International Conference on Fuzzy Systems.*

Tamura et al. Unsupervised learning method for a support vector machine and its application to surface electromyogram recognition. Artif Life Robotics (2009) 14:362-366.*

Winters-Hilt et al. SVM clustering. BMC Bioinformatics 2007, 8(Suppl 7):S18.*

Yang et al. A Kernel Fuzzy c-Means Clustering-Based Fuzzy Support Vector Machine Algorithm for Classification Problems With Outliers or Noises. IEEE Transactions on Fuzzy Systems, vol. 19, No. 1, Feb. 2011.*

Yin et al. Speech-Based Cognitive Load Monitoring System. 2008 IEEE International Conference on Acoustics, Speech and Signal Processing.*

Zhang et al. Hybrid-Data-Driven Fuzzy Recognition of Operator Cognitive State in Human-Machine Cooperative Control System. 13th IFAC Symposium on Large Scale. Jul. 7-10, 2013.*

Zhao K., Tian Y., Deng N. (2009) New Unsupervised Support Vector Machines. In: Shi Y., Wang S., Peng Y., Li J., Zeng Y. (eds) Cutting-Edge Research Topics on Multiple Criteria Decision Making. Communications in Computer and Information Science, vol. 35. Springer, Berlin, Heidelberg.*

Honda et al. Component-wise robust linear fuzzy clustering for collaborative filtering. International Journal of Approximate Reasoning 37 (2004) 127-144. (Year: 2004).*

Das et al. Stabilization of Cluster Centers over Fuzziness Control Parameter in Component-wise Fuzzy c-Means Clustering. 2013 IEEE International Conference on Fuzzy Systems. (Year: 2013).*

* cited by examiner

| RED | GREEN | BLUE | YELLOW | PINK |
| --- | --- | --- | --- | --- |
| ORANGE | BLUE | GREEN | BLUE | WHITE |
| GREEN | YELLOW | ORANGE | BLUE | WHITE |
| BROWN | RED | BLUE | YELLOW | GREEN |
| PINK | YELLOW | GREEN | BLUE | RED |

FIGURE 3A

| RED | GREEN | BLUE | YELLOW | PINK |
| --- | --- | --- | --- | --- |
| ORANGE | BLUE | GREEN | BLUE | WHITE |
| GREEN | YELLOW | ORANGE | BLUE | WHITE |
| BROWN | RED | BLUE | YELLOW | GREEN |
| PINK | YELLOW | GREEN | BLUE | RED |

FIGURE 3B

$x = 3;$
$if(x == 3)$
$then(y = 6);$
$if(y == 6)$
$then(z = 1);$
Problem: find $z$
Answer
i) $z = 1$
ii) $z = 0$
iii) $z \neq 1$

FIGURE 4A

Rule:
    Z=4
    if ~[(x>=2) or (y>3)] then z=z+1
    else if (y>2) then z=z-1

Problem: if output is z=3, then valid x is
    1. x=3
    2. x=2
    3. x=1

FIGURE 4B

SYSTEM AND METHOD FOR EVALUATING A COGNITIVE LOAD ON A USER CORRESPONDING TO A STIMULUS

PRIORITY CLAIM

This application is a national stage application under 35 U.S.C. § 371 of PCT/IB2014/064466 filed on 12 Sep. 2014 and published as WO/2015/040532 on 26 Mar. 2015 which claims priority to Indian patent application 3025/MUM/2013, filed on 19 Sep. 2013, which applications and publications are incorporated by reference as if reproduced herein and made a part hereof in their entirety, and the benefit of priority of each of which is claimed herein.

TECHNICAL FIELD

The present disclosure relates to a field of measurement of cognitive load. More particularly, the present disclosure relates to a system and method for evaluating the cognitive load on a user with respect to a stimulus.

BACKGROUND

The study of emotions in human-computer interaction has increased in recent years for variety of purposes. The study of emotions has led to a growing need for computer applications to detect cognitive load experienced by an individual. For a mental task given to the individual, the cognitive load experienced by different individuals is different. The measurement of cognitive load may be used in real-time personalized content generation for distant learning, customize and test various applications on mobile devices, and many other areas related to human interactions.

Electroencephalogram (EEG) signals are used to analyze the brain signals to measure the cognitive load for the individual. Conventional methods for measurement of cognitive load using EEG signals use a supervised approach. The methodology of using the EEG signals for measurement of the cognitive load may include issues related to change in intensity and signal range for a same individual for different trials. Also, the EEG signals may vary due to spatial shift in the positioning of the leads from one trial to another for the same individual.

Models generated for measurement of cognitive load using supervised learning approach may not address the issue of normalization related to the EEG signals unless the EEG signals are normalized before training. The supervised approach requires use of two step model generation requiring user training at two stages, which is time-consuming and tedious.

SUMMARY

Embodiments of the present disclosure present technological improvements as solutions to one or more of the above-mentioned technical problems recognized by the inventors in conventional systems. For example, in one implementation, a method for evaluating a cognitive load, on a user, corresponding to a stimulus is disclosed. The method comprises receiving electroencephalogram (EEG) data of the user. The EEG data is generated corresponding to the stimulus. The method further comprises splitting the EEG data into a plurality of slots. A slot of the plurality of slots comprises a subset of the EEG data. The method further comprises extracting one or more EEG features from the subset of the EEG data. The one or more EEG features are represented in one of a frequency domain, and a time domain. The method further comprises grouping a plurality of data points present in the one or more EEG features into two or more clusters using an unsupervised learning technique. The two or more clusters comprise one or more data points of the plurality of data points. The one or more data points correspond to a level of the cognitive load. The method of receiving, the splitting, the extracting, and the grouping are performed by a processor using programmed instructions stored in a memory.

In one implementation, a system for evaluating a cognitive load, on a user, corresponding to a stimulus is disclosed. The system comprises a processor and a memory coupled to the processor. The processor executes a plurality of modules stored in the memory. The plurality of modules comprises a receiving module to receive electroencephalogram (EEG) data of the user. The EEG data is generated corresponding to the stimulus. The plurality of modules further comprises a splitting module to split the EEG data into a plurality of slots. A slot of the plurality of slots comprises a subset of the EEG data. The plurality of modules further comprises an extracting module to extract one or more EEG features from the subset of the EEG data. The one or more EEG features are represented in one of a frequency domain and a time domain. The plurality of modules further comprises a grouping module to group a plurality of data points present in the one or more EEG features into two or more clusters using an unsupervised learning technique. The two or more clusters comprise one or more data points of the plurality of data points. The one or more data points correspond to a level of the cognitive load.

In one implementation, a non-transitory computer readable medium embodying a program executable in a computing device for evaluating a cognitive load, on a user, corresponding to a stimulus is disclosed. The program comprises a program code for receiving electroencephalogram (EEG) data of the user. The EEG data is generated corresponding to the stimulus. The program further comprises a program code for splitting the EEG data into a plurality of slots. A slot of the plurality of slots comprises a subset of the EEG data. The program further comprises a program code for extracting one or more EEG features from the subset of the EEG data. The one or more EEG features are represented in one of a frequency domain and a time domain. The program further comprises a program code for grouping a plurality of data points present in the one or more EEG features into two or more clusters using an unsupervised learning technique. The two or more clusters comprise one or more data points of the plurality of data points. The one or more data points correspond to a level of the cognitive load.

It is to be understood that both the foregoing general description and the following detailed description are exemplary and explanatory only and are not restrictive of the invention, as claimed.

BRIEF DESCRIPTION OF THE DRAWINGS

The accompanying drawings, which are incorporated in and constitute a part of this disclosure, illustrate exemplary embodiments and, together with the description, serve to explain the disclosed principles.

FIG. 3A and FIG. 3B illustrate Stroop test slides used for measuring the level of the cognitive load, in accordance with an exemplary embodiment of the present disclosure.

FIG. 4A and FIG. 4B illustrate logical reasoning test comprising logical questions for measuring the level of the cognitive load, in accordance with an exemplary embodiment of the present disclosure.

DETAILED DESCRIPTION

Exemplary embodiments are described with reference to the accompanying drawings. In the figures, the left-most digit(s) of a reference number identifies the figure in which the reference number first appears. Wherever convenient, the same reference numbers are used throughout the drawings to refer to the same or like parts. While examples and features of disclosed principles are described herein, modifications, adaptations, and other implementations are possible without departing from the spirit and scope of the disclosed embodiments. It is intended that the following detailed description be considered as exemplary only, with the true scope and spirit being indicated by the following claims.

The present subject matter discloses a system and method for evaluating a cognitive load, on a user, corresponding to a stimulus. Electroencephalogram (EEG) data corresponding to the stimulus given to the user is received. The stimulus corresponds to a mental task performed by the user. The EEG data is split into a plurality of slots. A slot of the plurality of slots comprises a subset of the EEG data. One or more EEG features are extracted from the subset of the EEG data. The one or more EEG features are represented in at least one of a frequency domain and a time domain. A plurality of data points present in the one or more EEG features is grouped into two or more clusters using an unsupervised learning technique. The two or more clusters comprise one or more data points of the plurality of data points. The one or more data points correspond to a level of the cognitive load.

The unsupervised learning technique comprises at least one of a Fuzzy c-Means algorithm, and a Component-wise Fuzzy c-Means algorithm. Use of the unsupervised learning technique to measure the levels of the cognitive load overcomes issues related to normalization of the EEG data.

While aspects of described system and method for evaluating a cognitive load, on a user, corresponding to a stimulus may be implemented in any number of different computing systems, environments, and/or configurations, the embodiments are described in the context of the following exemplary system.

Figure 1:
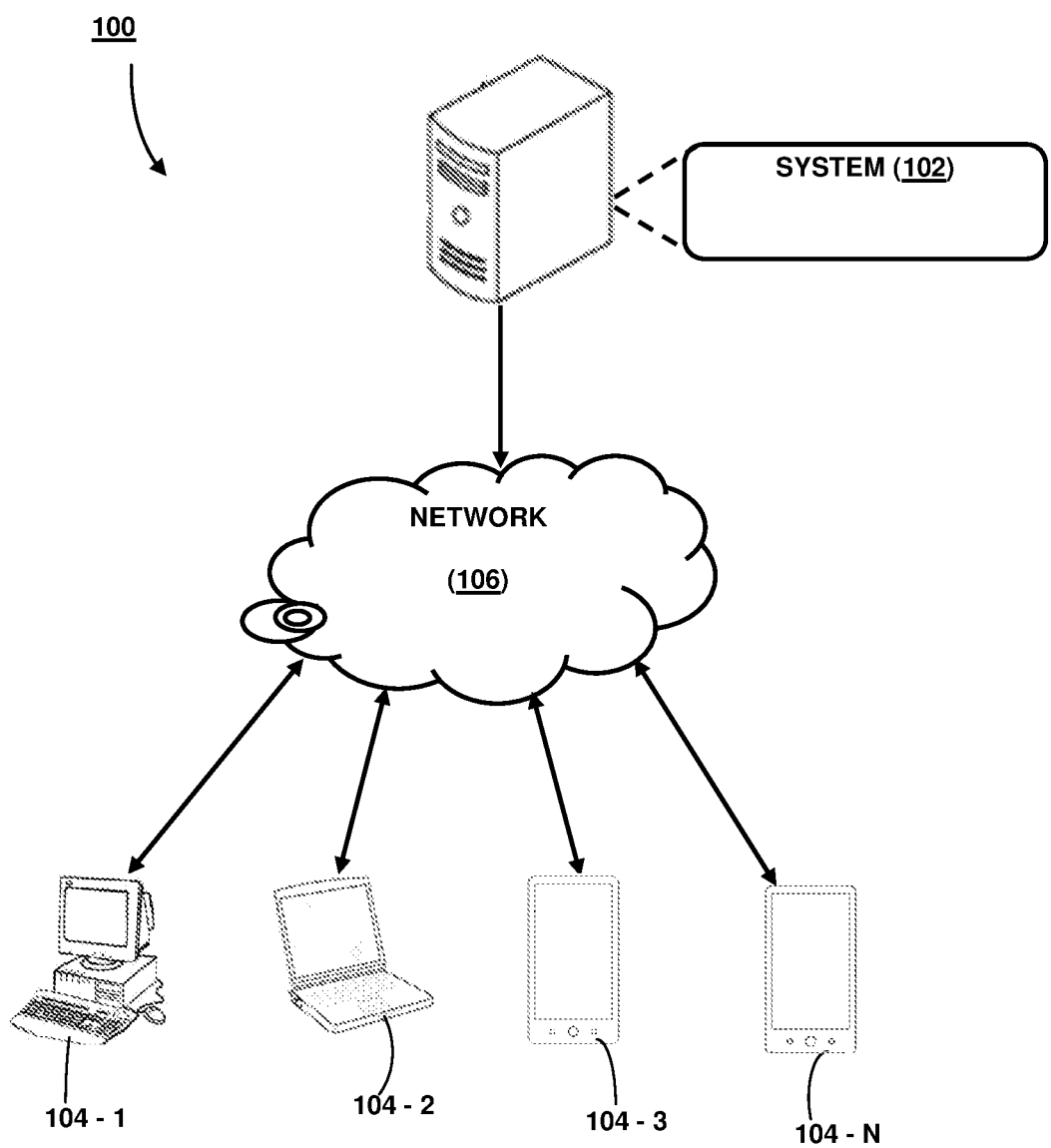
FIG. 1 illustrates a network implementation of a system for evaluating a cognitive load on a user, corresponding to a stimulus, in accordance with an embodiment of the present disclosure.

Referring now to FIG. 1, a network implementation 100 of a system 102 for evaluating a cognitive load, on a user, corresponding to a stimulus is illustrated, in accordance with an embodiment of the present disclosure.

Although the present disclosure is explained by considering a scenario that the system 102 is implemented as an application on a server, it may be understood that the system 102 may also be implemented in a variety of computing systems, such as a laptop computer, a desktop computer, a notebook, a workstation, a mainframe computer, a server, a network server, and the like. It will be understood that the system 102 may be accessed by multiple users through one or more user devices 104-1, 104-2 . . . 104-N, collectively referred to as user devices 104 hereinafter, or applications residing on the user devices 104. Examples of the user devices 104 may include, but are not limited to, a portable computer, a personal digital assistant, a handheld device, and a workstation. The user devices 104 are communicatively coupled to the system 102 through a network 106.

In one implementation, the network 106 may be a wireless network, a wired network or a combination thereof. The network 106 can be implemented as one of the different types of networks, such as intranet, local area network (LAN), wide area network (WAN), the Internet, and the like. The network 106 may either be a dedicated network or a shared network. The shared network represents an association of the different types of networks that use a variety of protocols, for example, Hypertext Transfer Protocol (HTTP), Transmission Control Protocol/Internet Protocol (TCP/IP), Wireless Application Protocol (WAP), and the like, to communicate with one another. Further the network 106 may include a variety of network devices, including routers, bridges, servers, computing devices, storage devices, and the like.

Figure 2:
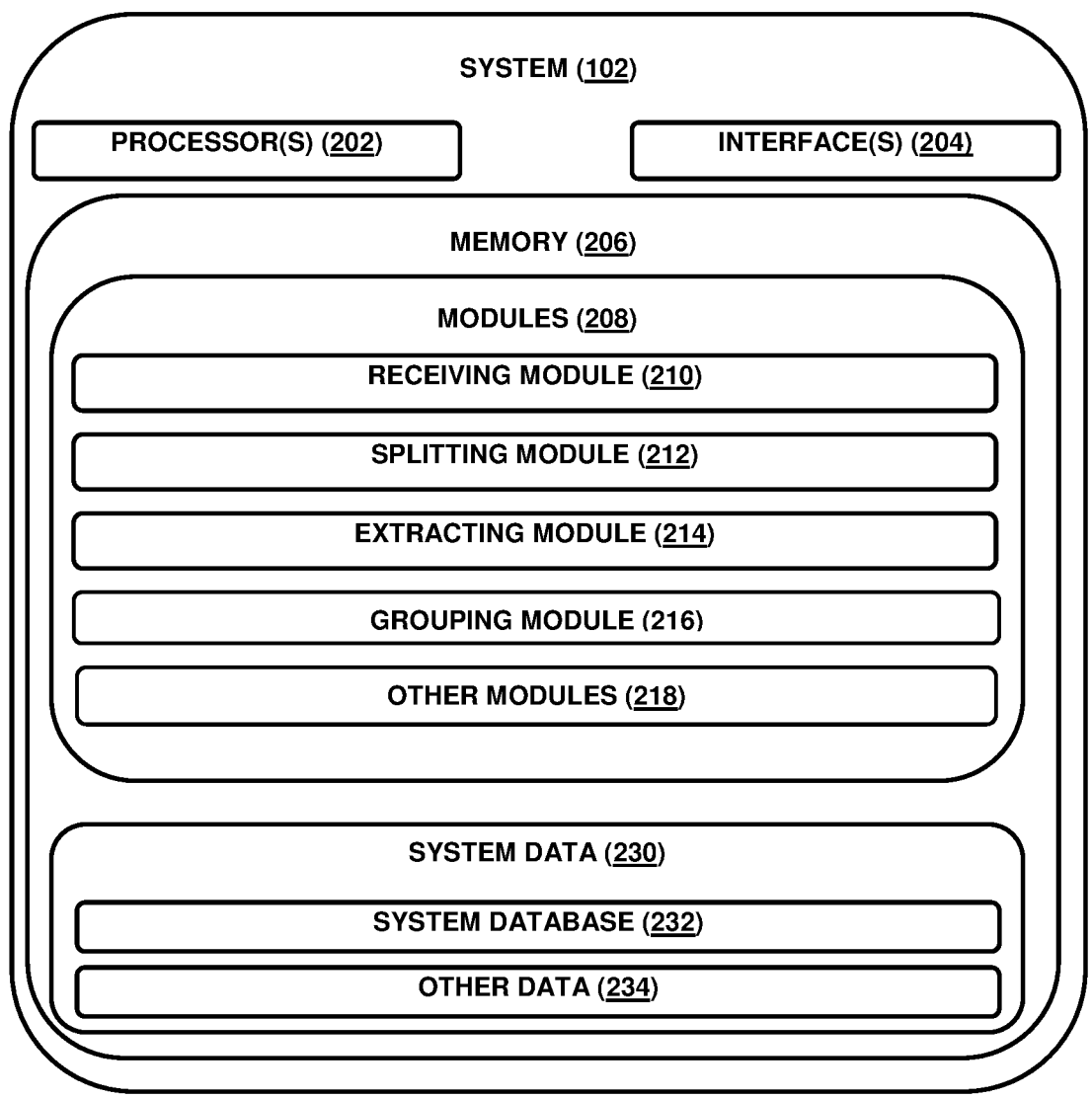
FIG. 2 illustrates the system, in accordance with an embodiment of the present disclosure.

Referring now to FIG. 2, the system 102 is illustrated in accordance with an embodiment of the present disclosure. In one embodiment, the system 102 may include at least one processor 202, an input/output (I/O) interface 204, and a memory 206. The at least one processor 202 may be implemented as one or more microprocessors, microcomputers, microcontrollers, digital signal processors, central processing units, state machines, logic circuitries, and/or any devices that manipulate signals based on operational instructions. Among other capabilities, the at least one processor 202 is configured to fetch and execute computer-readable instructions stored in the memory 206.

The I/O interface 204 may include a variety of software and hardware interfaces, for example, a web interface, a graphical user interface, and the like. The I/O interface 204 may allow the system 102 to interact with a user directly or through the user devices 104. Further, the I/O interface 204 may enable the system 102 to communicate with other computing devices, such as web servers and external data servers (not shown). The I/O interface 204 may facilitate multiple communications within a wide variety of networks and protocol types, including wired networks, for example, LAN, cable, etc., and wireless networks, such as WLAN, cellular, or satellite. The I/O interface 204 may include one or more ports for connecting a number of devices to one another or to another server.

The memory 206 may include any computer-readable medium known in the art including, for example, volatile memory, such as static random access memory (SRAM) and dynamic random access memory (DRAM), and/or non-volatile memory, such as read only memory (ROM), erasable programmable ROM, flash memories, hard disks, optical disks, and magnetic tapes. The memory 206 may include modules 208 and system data 230.

The modules 208 include routines, programs, objects, data structures, etc., which perform particular tasks or implement particular abstract data types. In one implementation, the modules 208 may include a receiving module 210, a splitting module 212, an extracting module 214, a grouping module 216 and other modules 218. The other modules 218 may include programs or coded instructions that supplement applications and functions of the system 102.

The system data 230, amongst other things, serves as a repository for storing data processed, received, and generated by one or more of the modules 208. The system data 230 may also include a system database 232 and other data 234. The other data 234 may include data generated as a result of the execution of one or more modules in the other modules 218.

In one implementation, at first, a user may use the client device 104 to access the system 102 via the I/O interface 204. The working of the system 102 may be explained in detail in FIGS. 2, and 3 explained below. The system 102 may be used for evaluating the cognitive load, on the user, corresponding to the stimulus. In order to evaluate the cognitive load, the system 102, at first, receives Electroencephalogram (EEG) data of the user. Specifically, in the present implementation, the EEG data is received by the receiving module 210.

In one embodiment, the receiving module 210 receives the EEG data of the user from an EEG device. The EEG device may be worn on head of the user to receive EEG signal. The EEG data represents the EEG signal generated corresponding to the stimulus of the user. The EEG data may comprise intensity and signal range variation among different users and the signal range variation for the same user for different experiments. The Intensity may vary for different users due to the shape of the head or scalp of different users. The signal range variation may occur due to spatial shift in positioning of leads of the EEG device from one experiment to another for the same user. The intensity and the signal range variation are referred to as issues related to normalization.

In one exemplary embodiment, the EEG data may be recorded using 14-channel Emotive neuro-headset. The EEG device may use a 10-20 electrode configuration for channel fixing. Sampling frequency of the EEG device may be set to 128 Hz.

The cognitive load may be defined as an amount of load experienced by working memory of the user to perform a task. The cognitive load may be classified into at least one of an Intrinsic load, an extraneous load, and a germane load. Type of the cognitive load may affect learning and decision making process of the user. The intrinsic load may refer to complexity of the task. The extraneous load may refer to an additional load caused by presentation method of the task. The germane load may refer to the load due to learning of a new technology or schema.

In one exemplary embodiment, based on the type of the cognitive load, the cognitive load on the user corresponding to the stimulus may be evaluated using at least one of a Stroop test, a Generic User Interface test, and a Logical reasoning test. The Stroop test and the Generic User Interface test may be used to evaluate the extraneous load. The logical reasoning test may be used to evaluate the germane load. The stimulus may impart two levels of complexity, i.e. low level of the cognitive load and high level of the cognitive load. The Stroop test, the Generic User Interface test, and the Logical reasoning test may be performed for generating the stimulus.

In one embodiment, in the Stroop test, the user may be asked to read colors of text presented on a slide while the user is wearing the EEG device. The Stroop test used for measuring the level of the cognitive load is illustrated in FIG. 3A and FIG. 3B. FIG. 3A illustrates the slide for the Stroop test measuring the low level of the cognitive load. In one exemplary embodiment, in order to measure the low level of the cognitive load, name of the colors printed in a color identified by the name may be shown to the user. FIG. 3B illustrates the slide for the Stroop test measuring the high level of the cognitive load. In one exemplary embodiment, in order to measure the high level of the cognitive load, a name printed in a color, which is not identified by the name may be shown to the user. For the above scenarios, the user may be asked to read the color denoted by the text instead of name of the color.

In one embodiment, for the Logical reasoning test, a set of logical reasoning questions having different levels of the cognitive load may be presented to the user. The questions comprising single logical error may be presented to impart the low level of the cognitive load. Further, the questions comprising multiple logical errors may be presented to impart the high level of the cognitive load. FIG. 4A and FIG. 4B illustrate the exemplary logical questions that may be presented to the user for measuring the low level of the cognitive load and the high level of the cognitive load respectively.

In one embodiment, in the Generic User Interface test, the user may be asked to type phrases using different onscreen keyboard layouts. For example, the user may be presented with a numerical keyboard comprising numbers and a QWERTY layout keyboard to type phrases comprising combination of numerical and alphabetic characters.

The EEG data may be received by the receiving module 210 as the EEG signals from the user performing the task. The EEG data received may be split into a plurality of slots. In one embodiment, the EEG data may be split by the splitting module 212. A slot of the plurality of slots may comprise a subset of the EEG data. In one embodiment, the subset of the EEG data may be received during a pre-defined time span. For example, the subset of the data may be received in a 10 second time span. In one embodiment, the subset of the EEG data may be filtered using a Common Spatial Pattern (CSP) Filter. In one embodiment, the subset of the EEG data may be filtered by a filtering module (not shown). In one exemplary embodiment, the subset of the EEG data may be fed as an input to the CSP filter to filter the subset of the EEG data based on variance of the subset of the EEG data.

The subset of the EEG data may comprise low spatial resolution. In order to overcome the low spatial resolution, the CSP filter may be used to maximize a variance of a band-pass filtered subset of the EEG data from a class of the subset of the EEG data and minimize the variance of the band-pass filtered subset of the EEG data from other class.

In one embodiment, one or more EEG features may be extracted from the subset of the EEG data. In one embodiment, the one or more EEG features may be extracted by the extracting module 214. The one or more EEG features may be represented in one of a frequency domain, and a time domain. The one or more EEG features may comprise one of a log variance, Hjorth parameters, and band power estimates. Further, the one or more EEG features may comprise at least one of entropy, or a gravity frequency, or wavelet coefficients. The one or more EEG features may comprise EEG features other than disclosed and use of such EEG features is obvious to a person skilled in the art. The one or more EEG features may be extracted to determine the level of the cognitive load imparted by the stimulus.

In one exemplary embodiment, the one or more EEG features may be extracted from the CSP filter channels after the subset of the EEG data i.e. the EEG signals are fed to the CSP filter. In one exemplary embodiment, the CSP filter channels may comprise 14 CSP channels. The following description describes a manner in which the one or more EEG features may be constructed. However, the construction of the one or more features other than embodiments disclosed is obvious to a person skilled in the art.

The one or more EEG features may be extracted as explained in the following embodiment. Let x[n] represent a time sample on one of the CSP filter channels output and X[t] a corresponding frequency domain representing the EEG signal for a given the slot, then Total Band Power (TBP) may be defined as:
TBP=$\Sigma_{i=f1}^{f2}X^2(fi)$ where, $f_1$ and $f_2$ may represent lower and upper cut-off frequencies for a particular EEG frequency band. In other words, all the frequency bins within the range of $f_1$ and $f_2$ may be squared and may be added to get a total power in a particular frequency band.

Different EEG frequency bands may be defined as:
Delta (δ) band (DB), where $f_1$=0 Hz and $f_2$=4 Hz
Theta (θ) band (TB), where $f_1$=4 Hz and $f_2$=8 Hz
Alpha (α) band (AB), where $f_1$=8 Hz and $f_2$=12 Hz
Beta (β) band (BB), where $f_1$=14 Hz and $f_2$=30 Hz
Gamma (γ) band (GB), where $f_1$=30 Hz and $f_2$=60 Hz Further, a Log Band Power Ratio (LBPR) may be defined as:

$$LBPR_{i,j} = \frac{\log(TBPi)}{\log(TBPj)}$$

where, i,j∈{DB, TB, AB, BB, GB} and i≠j where $TBP_i$ may denote (TBP) for the $i^{th}$ band and $TBP_j$ may denote (TBP) for the $j^{th}$ band.

Further, the EEG feature $F_j$ on the $i^{th}$ CSP output may be defined as $F_i$=$LBPR_{BB,TB}$, where i=1, 2 may be considered as first two CSP filter channels to compute the one or more EEG features.

In one exemplary embodiment, the CSP filter may be used to determine two most discriminative channels and to determine the EEG features corresponding to the two most discriminative channels. In one exemplary embodiment, an experiment may be performed without using the CSP filter. An unsupervised learning technique may be used to determine the one or more EEG features for all the channels.

In one embodiment, a plurality of data points present in the one or more EEG features may be grouped into two or more clusters using the unsupervised learning technique. The plurality of data points may be grouped by the grouping module 216. The two or more clusters may comprise one or more data points of the plurality of data points. The one or more data points may correspond to the level of the cognitive load. In one embodiment, the unsupervised learning technique comprises one of a Fuzzy c-Means (FCM) algorithm, or a Component-wise Fuzzy c-Means (CFCM) algorithm.

The one or more EEG features extracted may be grouped into two or more clusters based on a similarity of the one or more data points. In one embodiment, the one or more data points may be grouped into two or more clusters to partition the one or more data points. The one or more data points may be partitioned into non-overlapped clusters to determine a cluster center.

In one embodiment, the system 102 further comprises a labeling module to label the two or more clusters using the one or more EEG features corresponding to the cluster center to determine the level of the cognitive load. The one or more data points present in the one or more EEG features grouped into the two or more clusters using the unsupervised approach may result into a plurality of clusters with corresponding coordinates of cluster centers. Further, each cluster of the two or more clusters may be labeled by the labeling module (not shown).

In one embodiment, a formulation technique may be used to label the two or more clusters using the one or more EEG features of the cluster centers to determine the level of the cognitive load. For example, the formulation technique may include calculating ratios of 'Beta power' and 'Theta power' i.e. 'Beta power/Theta power' for the two or more clusters. The ratios of the 'Beta power' and 'Theta power' for the two or more clusters may be compared to determine the level of the cognitive load. The clusters comprising higher value may indicate the high level of the cognitive load. Further, the clusters comprising lower value may indicate the low level of the cognitive load. In one embodiment, the EEG data may be processed slot by slot. A cognitive score may be computed based on the plurality of slots and the plurality of slots comprising the subset of the EEG data corresponding to the level of the cognitive load. The level of the cognitive load may be indicative of difficulty of the mental task. Further, the cognitive score may be computed based on the plurality of slots and the plurality of slots comprising the subset of the EEG data corresponding to the high level of the cognitive load and the low level of the cognitive load.

In one embodiment, the cognitive score may be computed by a computing module (not shown in the figure). Further, size of the slot may be defined based on the cognitive score. In one exemplary embodiment, the size of the slot may be defined based on maximum discrimination of the cognitive score between the high level of the cognitive load and the low level of the cognitive load. The cognitive score may be used to determine the level of cognitive load. For example, consider the cognitive score to be in a range of 0 to 1 and a threshold level to be 0.5 in order to determine the level of the cognitive load. When the cognitive score is less than the threshold level i.e. 0.5, the cognitive load may be determined as the low level of the cognitive load. Further, when the cognitive score is more than the threshold level i.e. 0.5, the cognitive load may be determined as the high level of the cognitive load.

In one embodiment, the cognitive score may be computed based on a percentage of the slots i.e., number of slots reported as high for the observation. For example, if the observation comprises of N analysis slots and if M of the N slots are indicated as high, then the cognitive score for the observation may be calculated as:

Cognitive score=(M/N)×100%. Higher the cognitive score, higher may be the cognitive load imparted on the user for that particular observation. Similarly, lower the cognitive score indicate lower may be the cognitive load imparted on the user.

Further, in one embodiment, the FCM algorithm may be used to group the plurality of the data points into two or more clusters. Each data point of the plurality of data points may be induced by a membership value. The membership value is a function of distance measure of a data point from the cluster center. The FCM is an iterative process of finding the cluster center based on the membership value. For each of the iteration in the FCM algorithm, the membership value may be used for assignment of the one or more data points to one of the two or more clusters.

In the CFCM algorithm, instead of providing an overall membership value for the data point, each individual dimension of the data point may be assigned a membership value belonging to a cluster. Assigning a data point membership value to each dimension of the data point belonging to the cluster may lead to poor clustering due to odd parametric values of one or more dimensions. The assignment of the membership value may facilitate in improving the performance of the clustering. Further, the individual membership value belonging to a component level may be aggregated at the time of calculating the cluster center. The membership value may be aggregated instead of providing freedom to the data point.

In one embodiment, a fuzziness control parameter m may be determined for the cluster center using the CFCM algorithm. Further, the CFCM algorithm may update value of the fuzziness control parameter m based on stability criterion of the cluster center. The CFCM may tune the fuzziness control parameter m in stability region of the cluster centers irrespective of initial value of m. The implementation of the CFCM may be explained in greater detail in the following embodiments.

In one exemplary embodiment, a component wise independent membership value may be assigned based on an individual dimension of the data point to at least one cluster.

Let, $\vec{X} = \{\vec{x}_1, \vec{x}_2, \ldots \vec{x}_N\} \subset \mathfrak{R}^n$ be n dimensional input data of the size N, where $\mathfrak{R}$ is a n dimensional real number space.

Further, let $X_k^j$ denotes $j^{th}$ dimension or component of $k^{th}$ data point, where $1 \leq j \leq n$ and $1 \leq k \leq N$. $\vec{V} = \{\vec{v}_1, \vec{v}_2, \ldots, \vec{v}_c\} \subset \mathfrak{R}^n$ be n dimensional cluster centers, where c is the number of clusters for the input data $\vec{X}$.

Further, let $\mu_{Ai}(x_k^j)$ be the membership value of $x_k^j$ belonging to $i^{th}$ cluster $A_i$, where $1 \leq i \leq c$.

In the FCM, the membership value of $\vec{x}_k$ may belong to $i^{th}$ cluster given by $\mu_{Ai}(\vec{x}_k)$. However, in the CFCM, components of the data points may be assigned a membership value $\mu_{Ai}(x_k^j)$ as shown earlier.

In one embodiment, an objective function of the CFCM may be minimized using $$J = \sum_{k=1}^{N} \sum_{j=1}^{m} \sum_{i=1}^{c} [\mu_{Ai}(x_k^j)]^m (x_k^j - v_i^j)^2$$

subject to $$\sum_{i=1}^{c} \mu_{Ai}(x_k^j) = 1$$

for all the components $1 \leq j \leq n$ and for all the data points $1 \leq k \leq N$, where m is the fuzziness control parameter and $v_i^j$ denotes the $j^{th}$ dimension or component of the $i^{th}$ cluster center.

For the above, considering a constrained optimization problem, Lagrange's multiplier method may be used to formulate a minimization problem where it is equivalent to minimize $$L = \sum_{k=1}^{N} \sum_{j=1}^{m} \sum_{i=1}^{c} [\mu_{Ai}(x_k^j)]^m (x_k^j - v_i^j)^2 - \sum_{k=1}^{N} \sum_{j=1}^{m} \lambda_k^j \left( \sum_{i=1}^{c} \mu_{Ai}(x_k^j) - 1 \right),$$

considering partial derivatives of L with respect to $\mu_{Ai}(x_k^j)$, $v_i^j$ and $\lambda_i^j$. The partial derivations provide update rules for the cluster centers and the membership values for each of the component respectively.

In one embodiment, an initial value of cluster center may be calculated using the FCM algorithm. The new cluster centers for $v_i^j$ may be calculated using $$v_i^j = \frac{\sum_{k=1}^{N} [\mu_{Ai}(x_k^j)]^m \cdot x_k^j}{\sum_{k=1}^{N} [\mu_{Ai}(x_k^j)]^m}.$$

Further, the new membership value, $\mu_{Ai}(x_k^j)$ may be calculated using $$\mu_{Ai}(x_k^j) = \frac{\left((x_k^j - v_i^j)^2\right)^{\frac{-1}{m+1}}}{\sum_{i=1}^{c} \left((x_k^j - v_i^j)^2\right)^{\frac{-1}{m-1}}}.$$

The calculation of the cluster centers and the membership values may be iterated until a change in $\mu_{Ai}(x_k^j)$ is not negligible or the number of iterations have not reached a pre-defined limit.

In one embodiment, freedom provided to the components of each data point contributes independently to determine the cluster center. Further, the freedom provided to the components results in a fluctuation in the cluster centers over the iterations. The fluctuation may offer wider region of search of the cluster centers instead of getting stuck at a local optima. In the CFCM algorithm, the fluctuation in the cluster center may be stabilized by automatically adapting the fuzziness control parameter m towards its convergence, thereby allowing the CFCM algorithm to terminate with the stable cluster centers.

In one embodiment, the implementation of the CFCM algorithm may be modified by updating the fuzziness control parameter m based on cluster center stability criteria.

Further, the aggregation of the component memberships may be used to derive the cluster centers. The aggregation may be performed as a part of the minimization of the objective function of the CFCM algorithm, during updating of the cluster centers. The aggregation enables a binding between the individual memberships $\mu_{Ai}(x_k^j)$ and the aggregated memberships, $\mu_{Ai}^{agr}(\vec{x}_k)$ in each step of the iteration. The aggregation may be implemented using:

$$\mu_{Ai}^{agr}(\vec{x}_k) = \frac{1}{n} \sum_{j=1}^{n} [\mu_{Ai}(x_k^j)]^m$$

Further, calculation of the cluster centers may be modified using the aggregated membership values $\mu_{Ai}^{agr}(\vec{x}_k)$ using $$v_i^j = \frac{\sum_{k=1}^{N} [\mu_{Ai}^{agr}(\vec{x}_k)] \cdot x_k^j}{\sum_{k=1}^{N} [\mu_{Ai}^{agr}(\vec{x}_k)]}$$

In one exemplary embodiment, the stability of the cluster centers may be obtained by using the value of the fuzziness control parameter m that has minimum effect in changing of the cluster centers. The partial derivatives of the cluster centers $v_i^j$ may be performed with respect to the fuzziness control parameter m as shown below:

$$\frac{\partial v_i^j}{\partial m} = \frac{\partial}{\partial m}\left[\frac{\sum_{k=1}^{N} \mu_{Ai}^{agr}(\vec{x}_k) \cdot x_k^j}{\sum_{k=1}^{N} \mu_{Ai}^{agr}(\vec{x}_k)}\right] = \frac{\partial}{\partial m}\left[\frac{\sum_{k=1}^{N} x_k^j \cdot \frac{1}{n}\sum_{j=1}^{n}[\mu_{Ai}(x_k^j)]^m}{\sum_{k=1}^{N} \frac{1}{n}\sum_{j=1}^{n}[\mu_{Ai}(X_k^j)]^m}\right]$$

$$\frac{\partial v_j^j}{\partial m} = \frac{m \cdot \sum_{k=1}^{N} x_k^j \cdot \sum_{j=1}^{n}[\mu_{Ai}(x_k^j)]^{m-1}}{\sum_{k=1}^{N}\sum_{j=1}^{n}[\mu_{Aj}(x_k^j)]^m} -$$

$$\frac{m \cdot \left(\sum_{k=1}^{N} x_k^j \cdot \sum_{j=1}^{n}[\mu_{Ai}(x_k^j)]^m\right) \cdot \left(\sum_{k=1}^{N}\sum_{j=1}^{n}[\mu_{Ai}(x_k^j)]^{m-1}\right)}{\left(\sum_{k=1}^{N}\sum_{j=1}^{n}[\mu_{Ai}(x_k^j)]^m\right)^2}$$

For every iteration, the value of the fuzziness control parameter m may be chosen such that the value provides minimum absolute value of the derivative accumulated over all the components of the all the clusters.

$$m\_update = \underset{1.1 \leq m \leq 2.5}{\operatorname{argmin}}\left(abs\left(\sum_{i=1}^{c}\sum_{j=1}^{n}\frac{\partial v_i^j}{\partial m}\right)\right)$$

Further, in order to provide transition of the fuzziness control parameter m between successive iterations, the value of m may be updated as a weighted mean between a previous and a new value using the update factor $\alpha$ ($0 < \alpha < 1$).

$$m := \alpha \sqrt[4]{m} + (1-\alpha) \cdot m\_update$$

The value of $\alpha$ may be tuned to improve the accuracy of the cluster centers using standard datasets. In one exemplary embodiment, the value of $\alpha$ may be chosen as 0.95.

Figure 5:
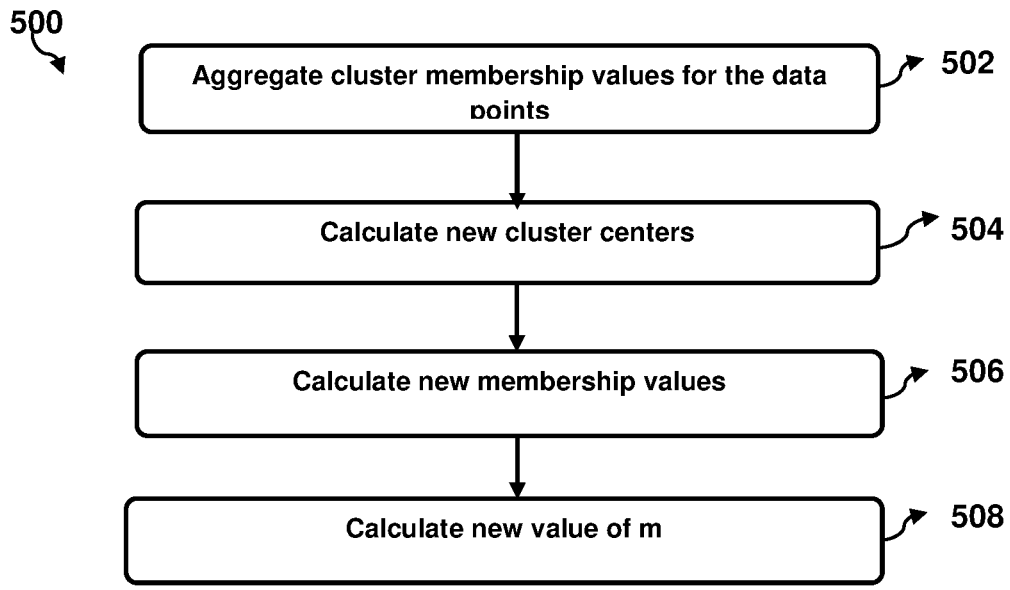
FIG. 5 illustrates a method for implementing Component-wise Fuzzy C-means (CFCM) algorithm, in accordance with an exemplary embodiment of the present disclosure.

In one embodiment, a method 500 for implementation of the CFCM algorithm is illustrated with the help of FIG. 5. The order in which the method 500 is described and is not intended to be construed as a limitation, and any number of the described method blocks can be combined in any order to implement the method 500 or alternate methods. Additionally, individual blocks may be deleted from the method 500 without departing from the spirit and scope of the disclosure described herein.

The method 500 comprises an initiation stage and an iterative update of the cluster centers and membership functions until termination criteria is not satisfied. The method 500 considers the data points as input $\vec{x}_k$ and the initial membership values $\mu_{Ai}(x_k^j)$. For every component of the data points belonging to the clusters i=1 to c, the initial value of the fuzziness control parameter m, the value of update factor $\alpha$ and $\epsilon$ as the termination criteria may be considered. The method 500 iteratively computes the new aggregated memberships $\mu_{Ai}^{agr}(\vec{x}_k)$. The method 500 further modifies the cluster centers $v_i^j$, modifies component-wise memberships $\mu_{Ai}(x_k^j)$, and modifies the fuzziness control parameter m. The method 500 terminates the iterative process when the sum of the absolute differences between the new memberships $^{new}\mu_{Ai}(x_k^j)$ and previous memberships $^{prev}\mu_{Ai}(x_k^j)$ in successive iterations is less than a pre-defined value $\epsilon$ or the number of iterations reaches a predefined limit.

When the iteration process completes, the final value of $v_i^j$ corresponds to the $j^{th}$ component of the $i^{th}$ cluster centers. Further, the value of $\mu_{Ai}(x_k^j)$ corresponds to the membership value of the $j^{th}$ component of the $k^{th}$ data points belonging to the $i^{th}$ cluster.

In one exemplary embodiment, the method 500 may be illustrated as follows:

Consider initial partitions $\mu_{Ai}(x_k^j)$ for i=1 to c clusters, j=1 to n components and k=1 to N data points. Consider $\vec{X}$ is the input data points, M is initial fuzziness control parameter the update factor $\alpha$ as 0.95 and $\epsilon$ is a small value as the termination criteria, for example 0.01.

At step 502, for k=1 to N and for i=1 to c, the aggregated memberships $\mu_{Ai}^{agr}(\vec{x}_k)$ may be calculated using, $$\mu_{Ai}^{agr}(\vec{x}_k) = \frac{1}{n}\sum_{j=1}^{n}[\mu_{Ai}(x_k^j)]^m.$$

At step 504, for k=1 to N, for i=1 to c and for j=1 to n, the cluster centers $v_i^j$ may be evaluated using, $$v_i^j = \frac{\sum_{k=1}^{N}[\mu_{Ai}^{agr}(\vec{x}_k)] \cdot x_k^j}{\sum_{k=1}^{N}[\mu_{Ai}^{agr}(\vec{x}_k)]}.$$

At step 506, for k=1 to N, for i=1 to c and for j=1 to n, the previous value $^{prev}\mu_{Ai}(x_k^j):\mu_{Ai}(x_k^j)$ may be stored. Further, if $((x_k^j - v_i^j)^2 > 0)$, the component wise membership $\mu_{Ai}(x_k^j)$ of the data points is evaluated using $$\mu_{Ai}(x_k^j) = \frac{\left((x_k^j - v_i^j)^2\right)^{\frac{-1}{m-1}}}{\sum_{i=1}^{c}\left((x_k^j - v_i^j)^2\right)^{\frac{-1}{m-1}}}$$

and the data points are named $^{new}\mu_{Ai}(x_k^j)$.

At step 508, the values may be set as $\mu_{Ai}(x_k^j) := 1$ by calling the values $^{new}\mu_{Ai}(x_k^j)$. Further, the values may be set as $\mu_{Ai}(x_k^j) := 0$ for $l \neq 1$ and by calling the new values $^{new}\mu_{Ai}(x_k^j)$. Further, the value of m may be updated as the weighted mean. A value corresponding to m_update value may be calculated using $$m\_update = \underset{1.1 \leq m \leq 2.5}{\operatorname{argmin}}\left(abs\left(\sum_{i=1}^{c}\sum_{j=1}^{n}\frac{\partial v_i^j}{\partial m}\right)\right) \text{ and }$$

-continued $$m := \alpha \cdot m + (1-\alpha) \cdot m\_update \text{ until } \sum_{k=1}^{N}\sum_{i=1}^{c}\sum_{j=1}^{n} |^{new}\mu_{Ai}(x_k^j) - {}^{prev}\mu_{Ai}(x_k^j)| < \varepsilon.$$

In one exemplary embodiment, the data points may be assigned to the cluster centers using the CFCM. The data points may be assigned to the cluster centers in order to compute an accuracy of the clustering with respect to the implementation of the CFCM. In one embodiment, the assignment of the data points to the cluster centers may be performed using a decision based on a binary rank matrix $(M_{ij}(\vec{x}_k))$ and a membership rank matrix $(U_{Ai}(\vec{x}_k))$. Entries of $(M_{ij}(\vec{x}_k))$ may be defined by $(M_{ij}(\vec{x}_k))=1$ if $i=1_k^j$ and $(M_{ij}(\vec{x}_k))=0$ if $i \neq 1_k^j$, where $1_k^j = \arg_{1 \leq i \leq c}\max(\mu_{Ai}(x_k^j))$, and $1_k^j$ may denote a cluster index for which the $j^{th}$ component of the $k^{th}$ data points comprising maximum membership.

The elements of the membership rank matrix $U_{Ai}(\vec{x}_k)$ may be defined as the average membership of the dimensions (j) of the data point for which $M_{ij}(\vec{x}_k)$ equals to 1. In one embodiment, the average membership may be determined using $$U_{Ai}(\vec{x}_k) = \frac{\sum_{j=1}^{n} \mu_{Ai}(x_k^j) \cdot M_{ij}(\vec{x}_k)}{\sum_{j=1}^{n} M_{ij}(\vec{x}_k)}.$$

The cluster index $(C_k^{data})$ corresponding to the data point k may be defined as the index $(1 \leq i \leq c)$ which has the maximum number of 1s in the binary rank matrix $M_{ij}(\vec{x}_k)$. The cluster index $C_k^{data}$, and may be presented as follows:

$$C_k^{data} = \operatorname*{argmax}_{1 \leq i \leq c}\left(\sum_{j=1}^{n} M_{ij}(\vec{x}_k)\right)$$

If more than one cluster index exists having same value of $$\sum_{j=1}^{n} M_{ij}(\vec{x}_k),$$

then the cluster index may be computed as $C_k^{data} = \arg_{1 \leq i \leq c}\max(\mu_{Ai}(x_k^j))$.

Due to the component-wise membership assignment in the CFCM, dimensionality may be reduced by tracking the components that may follow the data points compared to other components. A metric may be defined to measure how the components follow the parent data points. In order to define measurement of the metric, the cluster index of $k^{th}$ data points $C_k^{data}$ may be defined as $$C_k^{data} = \operatorname*{argmax}_{1 \leq i \leq c}\left(\sum_{j=1}^{n} M_{ij}(\vec{x}_k)\right) \text{ and } C_k^{data} = \operatorname*{argmax}_{1 \leq i \leq c}(\mu_{Ai}(x_k^j)).$$

Further, the cluster index $C_k^j$ of the $i^{th}$ component of the $k^{th}$ data points may be defined as the index $(1 \leq i \leq c)$ using:

$$C_k^j = \arg_{1 \leq i \leq c}(M_{ij}(\vec{x}_k) == 1).$$

Cluster indices $C_k^j$ for all the components j and $C_k^{data}$ for the data point k may be computed for each iteration. In one embodiment, the measurement metric may be defined as a goodness measure $G_k^j$ for each component of the data point. The measurement metric is equal to 1 if the cluster index for the data point is same as the cluster index of the component of the data point; else the measurement metric is 0. The accumulated goodness measure $G^j$ may be presented as $$G_k^j = 1, \text{ if } C_k^j = C_k^{data} \text{ and } G_k^j = 0, \text{ if } C_k^j \neq C_k^{data} \text{ and}$$

$$G^j = \sum_{k=1}^{N} G_k^j.$$

The accumulated goodness measure $G^j$ is sum of the goodness measure for all the data points. The values of $G^j$ may be computed for each of the iteration. Higher the value of goodness measure $G^j$, indicates that the component j follows the data points effectively. Further, higher the value of goodness measure $G^j$ results insignificance of the corresponding component. The dimensionality may be reduced by considering the set of components having higher values of $G^j$ at the end of the iteration process in the CFCM.

In one embodiment, the measurement metric may be used for performance analysis of the FCM algorithm, CFCM algorithm, and a Support Vector Machine (SVM). The selection of Fuzziness Control parameter m and the convergence over iterations using the CFCM algorithm and the performance comparison of Supervised SVM and Unsupervised FCM algorithm and the CFCM algorithm while classifying the EEG data into two levels of cognition load is presented. The performance metric used for analyzing output of both supervised and unsupervised technique is $F_{measure}$ defined as the harmonic mean of precision (P) and recall (R). The $F_{measure}$ is presented as $$F_{measure} = \frac{2 \cdot P \cdot R}{P + R}.$$

The precision (P) may be defined as the ratio of number of the data points belonging to a cluster (TP) and the total number of the data points identified to belong to the same cluster (TP+FP). FP represents false positive, i.e. total number of the data points that might have been falsely identified belonging to the cluster. The precision may be calculated using:

$$P = \frac{TP}{TP + FP}.$$

The recall (R) is the ratio of true positive (TP) and the total number of data points that actually belong to the cluster (TP+FN). Where the false negative FN, is the total number of data points which are wrongly identified as not belonging to the same cluster. The Recall may be calculated using:

$$R = \frac{TP}{TP+FN}.$$

Although the embodiments have been explained for evaluating two levels of clustering, it is understood that the disclosure can be implemented for multi-level cognitive load measurement.

Figure 6:
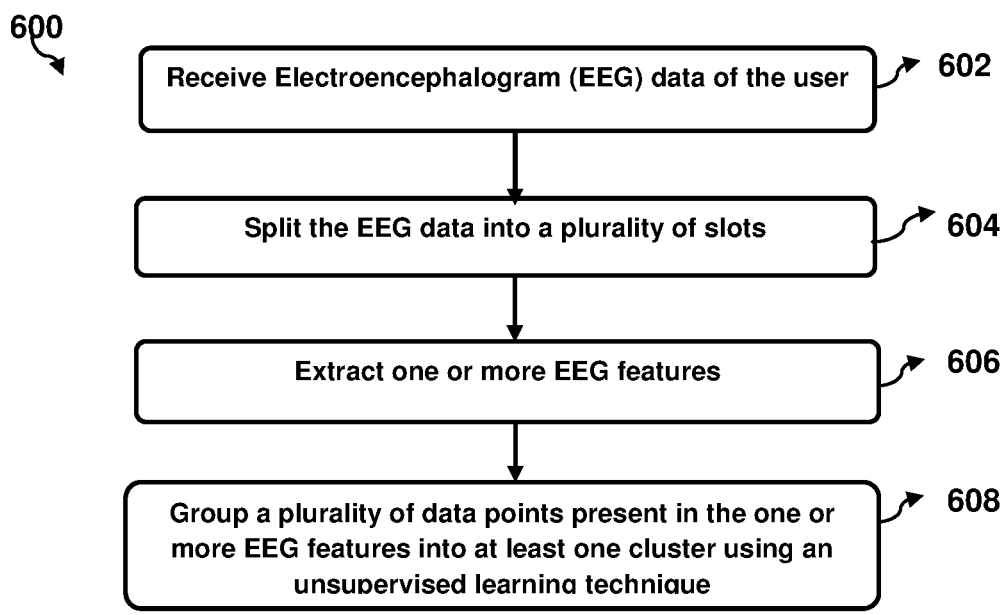
FIG. 6 illustrates a method for evaluating the cognitive load, on the user, corresponding to the stimulus, in accordance with an embodiment of the present disclosure.

Referring now to FIG. 6, a method 600 for evaluating a cognitive load on a user, corresponding to a stimulus is shown, in accordance with an embodiment of the present disclosure. The method 600 may be described in the general context of computer executable instructions. Generally, computer executable instructions can include routines, programs, objects, components, data structures, procedures, modules, functions, etc., that perform particular functions or implement particular abstract data types. The method 600 may also be practiced in a distributed computing environment where functions are performed by remote processing devices that are linked through a communications network. In a distributed computing environment, computer executable instructions may be located in both local and remote computer storage media, including memory storage devices.

The order in which the method 600 is described and is not intended to be construed as a limitation, and any number of the described method blocks can be combined in any order to implement the method 600 or alternate methods. Additionally, individual blocks may be deleted from the method 600 without departing from the spirit and scope of the disclosure described herein. Furthermore, the method may be implemented in any suitable hardware, software, firmware, or combination thereof. However, for ease of explanation, in the embodiments described below, the method 600 may be implemented in the above-described system 102.

At step 602, the Electroencephalogram (EEG) data of the user is received. The EEG data is generated corresponding to the stimulus. In one implementation, the Electroencephalogram (EEG) data of the user is received by the receiving module 210.

At step 604, the EEG data is split into a plurality of slots. A slot of the plurality of slots comprises a subset of the EEG data. In one implementation, the EEG data is split by the splitting module 212.

At step 606, one or more EEG features are extracted from the subset of the EEG data. The one or more EEG features are represented in one of a frequency domain and a time domain. In one implementation, the one or more EEG features are extracted by the extracting module 214.

At step 608, a plurality of data points present in the one or more EEG features are grouped into at least one cluster using an unsupervised learning technique. The at least one cluster comprises one or more data points of the plurality of data points. The one or more data points correspond to a level of the cognitive load. In one implementation, the plurality of data points is grouped by the grouping module 216.

Although implementations of system and method for evaluating cognitive load on a user, corresponding to the stimulus have been described in language specific to structural features and/or methods, it is to be understood that the appended claims are not necessarily limited to the specific features or methods described. Rather, the specific features and methods are disclosed as examples of implementations for evaluating cognitive load on the user.

The illustrated steps are set out to explain the exemplary embodiments shown, and it should be anticipated that ongoing technological development will change the manner in which particular functions are performed. These examples are presented herein for purposes of illustration, and not limitation. Further, the boundaries of the functional building blocks have been arbitrarily defined herein for the convenience of the description. Alternative boundaries can be defined so long as the specified functions and relationships thereof are appropriately performed. Alternatives (including equivalents, extensions, variations, deviations, etc., of those described herein) will be apparent to persons skilled in the relevant art(s) based on the teachings contained herein. Such alternatives fall within the scope and spirit of the disclosed embodiments. Also, the words "comprising," "having," "containing," and "including," and other similar forms are intended to be equivalent in meaning and be open ended in that an item or items following any one of these words is not meant to be an exhaustive listing of such item or items, or meant to be limited to only the listed item or items. It must also be noted that as used herein and in the appended claims, the singular forms "a," "an," and "the" Include plural references unless the context clearly dictates otherwise.

Furthermore, one or more computer-readable storage media may be utilized in implementing embodiments consistent with the present disclosure. A computer-readable storage medium refers to any type of physical memory on which information or data readable by a processor may be stored. Thus, a computer-readable storage medium may store instructions for execution by one or more processors, including instructions for causing the processor(s) to perform steps or stages consistent with the embodiments described herein. The term "computer-readable medium" should be understood to include tangible items and exclude carrier waves and transient signals, i.e., be non-transitory. Examples include random access memory (RAM), read-only memory (ROM), volatile memory, nonvolatile memory, hard drives, CD ROMs, DVDs, flash drives, disks, and any other known physical storage media.

It is intended that the disclosure and examples be considered as exemplary only, with a true scope and spirit of disclosed embodiments being indicated by the following claims.

We claim:

1. A method for evaluating a cognitive load, on a user, corresponding to a stimulus, the method comprising:
    receiving electroencephalogram (EEG) data of the user, wherein the EEG data is generated corresponding to the stimulus;
    splitting the EEG data into a plurality of slots, wherein a slot of the plurality of slots comprises a subset of the EEG data;
    extracting EEG features from the subset of the EEG data, wherein the EEG features are represented in one of a frequency domain and a time domain;
    computing a cognitive score as a percentage of a number of slots within the plurality of slots reported as a high level of cognitive load within a total number of the plurality of slots; and
    grouping a plurality of data points present in the EEG features into two or more clusters using an unsupervised learning technique, wherein the two or more clusters comprise one or more data points corresponding to a level of the cognitive load; wherein the cognitive load is based on the cognitive score, computed as a percentage of a number slots reported as a high level of the cognitive load by the user within a total number of the plurality of slots;

wherein the unsupervised learning technique comprises a Component-wise Fuzzy c-Means algorithm, and wherein the receiving, the splitting, the extracting and the grouping are performed by a processor using programmed instructions stored in a memory.

2. The method of claim 1, further comprising filtering the subset of the EEG data using a Common Spatial Pattern (CSP) Filter.

3. The method of claim 1, wherein the EEG features comprises one of a log variance, Hjorth parameters, and band power estimates.

4. The method of claim 1, wherein the stimulus corresponds to a mental task performed by the user.

5. The method of claim 1, wherein a level of the cognitive load is a level of difficulty of a mental task, and wherein the level of the cognitive load comprises one of the high level, and a low level depending on the cognitive score.

6. The method of claim 5, wherein the high level of the cognitive load is determined when the cognitive score is more than a threshold level.

7. The method of claim 5, wherein the low level of the cognitive load is determined when the cognitive score is less than a threshold level.

8. The method of claim 1, wherein the subset of the EEG data is received during a pre-defined time span.

9. A system for evaluating a cognitive load, on a user, corresponding to a stimulus, the system comprising:
a processor; and
a memory coupled to the processor, wherein the processor executes a plurality of modules stored in the memory, and wherein the plurality of modules comprising:
a receiving module configured to receive electroencephalogram (EEG) data of the user, wherein the EEG data is generated corresponding to the stimulus;
a splitting module configured to split the EEG data into a plurality of slots, wherein a slot of the plurality of slots comprises a subset of the EEG data;
an extracting module configured to extract EEG features from the subset of the EEG data, wherein the EEG features are represented in one of a frequency domain and a time domain;
a computing module configured to compute a cognitive score as a percentage of a number of slots within the plurality of slots reported as a high level of cognitive load within a total number of the plurality of slots; and
a grouping module configured to group a plurality of data points present in the EEG features into two or more clusters using an unsupervised learning technique, wherein the two or more clusters comprise one or more data points corresponding to a level of the cognitive load; wherein the cognitive load is based on the cognitive score, computed as a percentage of a number slots reported as a high level of the cognitive load by the user within a total number of the plurality of slots; and wherein the unsupervised learning technique comprise a Component-wise Fuzzy c-Means algorithm.

10. The system of claim 9, wherein the system further comprises a filtering module to filter the subset of the EEG data using a Common Spatial Pattern (CSP) Filter.

11. The system of claim 9, wherein the EEG features comprises one of a log variance, Hjorth parameters, and band power estimates.

12. A non-transitory computer readable medium embodying a program executable in a computing device for evaluating a cognitive load, on a user, corresponding to a stimulus, the program comprising:
a program code for receiving electroencephalogram (EEG) data of the user, wherein the EEG data is generated corresponding to the stimulus;
a program code for splitting the EEG data into a plurality of slots, wherein a slot of the plurality of slots comprises a subset of the EEG data;
a program code for extracting EEG features from the subset of the EEG data, wherein the one or more EEG features are represented in one of a frequency domain and a time domain; and
a program code for grouping a plurality of data points present in the EEG features into two or more clusters using an unsupervised learning technique, wherein the two or more clusters comprise one or more data points corresponding to a level of the cognitive load; wherein the program code evaluates the cognitive load by computing a cognitive score;
wherein the cognitive score is computed as a percentage of a number slots reported as a high level of the cognitive load within a total number of the plurality of slots.

* * * * *